United States Patent [19]
Walbrink et al.

[11] Patent Number: 5,514,089
[45] Date of Patent: May 7, 1996

[54] IRRIGATOR/ASPIRATOR SURGICAL PROBE AND VALVE ASSEMBLY

[75] Inventors: Harold J. Walbrink, Laguna Niguel; Roger F. Etherington, Newport Beach; Charles E. Beuchat, Irvine; Vincent J. Burgess, Laguna Niguel; Kent D. Richards, Santa Barbara, all of Calif.

[73] Assignee: Birtcher Medical Systems, Inc., Utica, N.Y.

[21] Appl. No.: 195,689

[22] Filed: Feb. 16, 1994

Related U.S. Application Data

[62] Division of Ser. No. 958,931, Oct. 9, 1992, abandoned.

[51] Int. Cl.$^6$ ........................................... A61H 1/00
[52] U.S. Cl. ........................ 604/33; 604/21; 604/35; 604/119
[58] Field of Search ........................ 604/21, 27, 30–32, 604/35, 119, 902; 433/91, 95, 96

[56]  References Cited

U.S. PATENT DOCUMENTS

| | | | |
|---|---|---|---|
| 4,519,385 | 5/1985 | Atkinson et al. | 604/27 X |
| 4,703,775 | 11/1987 | Pastrone | 137/625.3 |
| 5,186,714 | 2/1993 | Boudreault et al. | 604/21 |
| 5,224,929 | 7/1993 | Remiszewski | 604/30 |
| 5,295,956 | 3/1994 | Bales et al. | 604/30 |
| 5,347,992 | 9/1994 | Pearlman et al. | 128/4 |
| 5,348,555 | 9/1994 | Zinnanti | 606/49 |

*Primary Examiner*—Corrine McDermott
*Attorney, Agent, or Firm*—John R. Ley; John B. Phillips

[57]  ABSTRACT

An irrigator/aspirator surgical probe for laparoscopic surgery includes a rotatable handle assembly and a probe assembly having an electrosurgical electrode. The handle assembly has two valves, one for controlling the flow of irrigation fluid and one for controlling the flow of aspiration fluid. One of the valves can be locked at any selected setting with a locking lever. Fine adjustment of the valve is achieved in the locked position. The handle assembly further includes a valve body and valve members which are easily removable and disposable. The valve members in the valve body are made of an elastomeric material to provide effective sealing and inherent self return. The probe assembly can be rotated relative to the handle assembly as needed to reduce operator fatigue. The probe can be rotated in the probe assembly to position the electrode.

19 Claims, 7 Drawing Sheets

Fig_1

Fig_2

Fig_5

Fig_6

Fig_7

Fig_9

Fig_7A

Fig_8

Fig_10

Fig_11

Fig_12

Fig_13

Fig_14

Fig_15

IRRIGATOR/ASPIRATOR SURGICAL PROBE AND VALVE ASSEMBLY

CROSS REFERENCE TO RELATED APPLICATION

This is a division of U.S. patent application Ser. No. 07/958,931, filed Oct. 9, 1992 now abandoned.

FIELD OF THE INVENTION

The present invention relates to laparoscopic surgery and more particularly, to a new and improved minimally invasive surgical probe used to perform surgery and irrigate and aspirate within the interior of the human body.

BACKGROUND OF THE INVENTION

Three common types of surgery are typically performed internally within the human body. The traditional open type of surgery involves a large incision through the skin and muscle layers of the patient. The incision is made sufficiently large enough both to allow the surgeon to see into the body and to accommodate the surgeon's hands and instruments. Open surgery is sometimes referred to as invasive surgery.

A second type of surgery, endoscopy, involves inserting a flexible instrument through an existing body orifice to gain access to a passageway in the body such as the trachea, colon, or esophagus. The flexible instrument is typically in the form of a tube containing, at a minimum, a light source, an optical sensor, and a surgical tool such as a scalpel, an electrosurgical probe or a laser light channel. Since no incisions are made in the body, endoscopy is referred to as minimally invasive surgery.

A third related type of surgery is laparoscopy which involves cutting one or more small incisions to gain access to an internal cavity such as the abdominal cavity. To perform laparoscopic surgery in the abdominal cavity, two incisions are made through the abdominal wall of the patient. A plastic sleeve or cannula is inserted into both incisions. One cannula is attached to a gas pump, known as an insufflator. The insufflator pumps gas into the abdomen to expand the abdominal wall above the internal organs and create a cavity within which the surgical procedure is performed. Both cannulas allow instruments to be inserted into the abdominal cavity, manipulated to accomplish the surgical procedure and removed without further injury to the patient's skin and muscle layers. A light source and optical sensor are usually inserted through one of the cannulas. With the light source and sensor, the surgeon watches a video monitor to see the interior of the abdominal cavity. At the conclusion of the procedure, the instruments are removed, the abdominal cavity is deflated and the cannulas are removed. The only remaining outward effects of surgery are the two small incisions. For this reason, laparoscopy is also referred to as minimally invasive surgery.

It is common during minimally invasive surgery to deliver gas or liquid to irrigate the surgical site and wash away debris or other fluid. Aspiration is also typically used to remove smoke, debris or fluids such as blood or mucus. Aspiration involves suctioning gas, liquid and debris away from the surgical site and out of the body. Irrigation and aspiration are accomplished by placing the distal end of a tube at the surgical site and delivering fluid to the site or sucking fluid or other material away from the surgical site, by creating a positive or a negative pressure at the distal end of the tube, respectively.

The flow of fluid during irrigation and aspiration is typically controlled by the surgeon manually depressing valves which are located in a handle attached to the tube or which are associated with the tube. The tube and the handle are sometimes referred to as the probe. Such valves, which commonly use sliding O-rings to create seals, have several disadvantages. O-rings, when not in use, such as during storage and shipping to a hospital, may become stuck to the surrounding passageway or become flattened thereby causing an ineffective seal. The initial use of an instrument with O-rings may, therefore, be erratic and unsatisfactory. Further, the O-rings may not slide easily, causing difficulty in control and operator fatigue. Debris passing through the valves during aspiration may interfere with proper sealing.

During surgery the surgeon may experience distraction or discomfort from holding the probe in an awkward position or while holding down the valve control buttons on the probe. The relatively long instruments which must be manipulated during minimally invasive surgery may require some degree of added effort and facility to manipulate. The surgeon often is required to hold the handle in unusual or uncomfortable positions above the patient while performing the procedure. Holding the valve control buttons in a fixed position for a long period of time may cause discomfort. Since the fingers must firmly hold the control buttons in a fixed position, the instrument cannot be easily shifted around and re-gripped during the procedure, without releasing the control buttons.

Minimally invasive irrigator/aspirator probes may either be reusable or disposable after a single procedure. Disposable instruments are sometimes regarded as desirable because of the inconvenience of having to sterilize the instrument before each use. Autoclaving is the typical method of sterilizing an instrument and it involves placing the instruments in an oven-like device to heat them to an elevated temperature under pressure for a period of time to eliminate all of the bacteria and viruses on or in the instrument. Although disposing of surgical instruments after a single use may be regarded as an unnecessary expense, the autoclaving procedure itself involves the expense of human salary and time. Some surgical instruments are so expensive that they are only available as reusable instruments. Further, some surgical instruments are so complex that they must be disassembled for autoclaving and then reassembled afterwards. The assembly and disassembly procedure also adds to the cost of use of such instruments.

Minimally invasive irrigator/aspirator surgical probes present issues relating to both dispensable instruments and reusable instruments. The complex valve structure which may contain debris from aspiration is particularly difficult to sterilize without time consuming disassembly of the probe. Other pares of the probe can easily be autoclaved.

It is against this background information, and the desire to produce a more convenient minimally invasive surgical probe, that the present invention has resulted.

SUMMARY OF THE INVENTION

The present invention offers many significant improvements for a surgical probe which includes a valve assembly to control the flow of irrigation and/or aspiration fluid through an elongated probe tube. The probe tube is inserted into a body cavity during a laparoscopic surgical procedure and a surgical instrument is inserted through the hollow probe tube to perform a surgical procedure at a surgical site at a distal end of the probe tube. Preferably, the surgical instrument is an electrode by which electrical energy is conducted to the surgical site to achieve electrosurgery.

One of the improvements available from the present invention relates to a handle which extends at a predetermined converging or perpendicular angle relative to the probe tube. The handle is rotatably connected relative to the probe tube to allow the surgeon to position the handle in a comfortable and effective position during the laparoscopic surgical procedure. The valve assembly is preferably located in the handle, and the same position of the surgeon's hand relative to the actuation devices which control the valves in the valve assembly is maintained while the handle is rotated.

Another improvement available from the present invention relates to a locking device connected to the handle. The surgeon may selectively engage the locking device with one of the valve members and to hold the valve member in a selected open position. This locking device is preferably used in conjunction with the flow of aspiration fluid. By engaging the locking device, a continual flow of aspiration fluid at the surgical site is available without the discomfort of the surgeon having to continually depress the actuation device associated with the valve.

Another improvement available from the present invention relates to the valve assembly. Preferably, the valve assembly is removable from the handle. With the valve assembly removed, the remaining parts of the surgical probe can be more easily sterilized in an autoclave procedure, for example. The removable valve assembly itself can be disposed of and a new sterile valve assembly inserted in the remaining portion of the surgical probe at the time the surgical probe is again used in a laparoscopic surgical procedure.

A further improvement available from the present invention relates to the use of an elastomeric valve member in the valve assembly. The elastomeric valve member is particularly advantageous in deforming around particles and items of debris which might be lodged in the valve itself. By deforming around the debris, the elastomeric valve will generally achieve an adequate fluid seal to terminate the flow of irrigation or aspiration fluid, even though a small piece of debris might otherwise prevent full closure of the valve.

A further improvement available from the present invention relates to a rotational capability of the probe tube. The probe tube is preferably attached to a support member which is rotatably connected within a probe body. A connector is operative between the probe body and the support member to selectively permit and prevent rotation of the support member and the connected probe tube. By rotation of the probe tube, the medical instrument extending from the distal end of the probe tube may be more conveniently positioned during the surgical procedure, rather than requiring the surgeon to rotate the whole probe assembly.

Yet another improvement of the present invention is the capability of removing an elongated electrode assembly, when such an assembly is used as the medical instrument within the probe tube. Preferably the electrode assembly includes an elongated electrode to which an insert is connected at a rear end thereof. The insert contacts the support member, and the support member includes an interior channel through which the electrode extends when located within the hollow interior space of the probe tube. A connector, such as the connector which retains the support member and the probe tube to the probe body to permit and prevent relative rotation, may also contact the insert and maintain the electrode assembly in position within the probe.

A more complete understanding and appreciation of the present invention can be obtained by reference to the accompanying drawings, which are briefly described below, from the following detailed description of the presently preferred embodiment, and from the following claims.

DETAILED DESCRIPTION OF THE DRAWINGS

DESCRIPTION OF THE PREFERRED EMBODIMENT

An irrigator/aspirator surgical probe 20 incorporating the present invention is shown in FIGS. 1, 2, 3 and 15 to include a handle assembly 22 and a probe assembly 24. The handle assembly 22 includes a handle 26, a valve assembly 28 having two valves located within a hollow interior 30 (FIG. 5) of the handle 26, two control buttons 32 and 34 which protrude from the handle 26 and which control the operation of the valves of valve assembly 28, a locking lever 36 which may be selectively engaged to keep the control button 34 depressed, and connection ports 38 and 40 on the end of the valve assembly 28 by which to connect the surgical probe 20 to a suction pump 42 and a fluid delivery pump 44 by flexible hoses 46 and 48. The probe assembly 24 includes a probe body 50, a probe tube 52 extending from the probe body 50, an electrosurgical electrode 53 or other elongated medical surgical instrument located within the probe tube 52, and a connection for an electrical cable 54 to the electrode 53.

Figure 1:
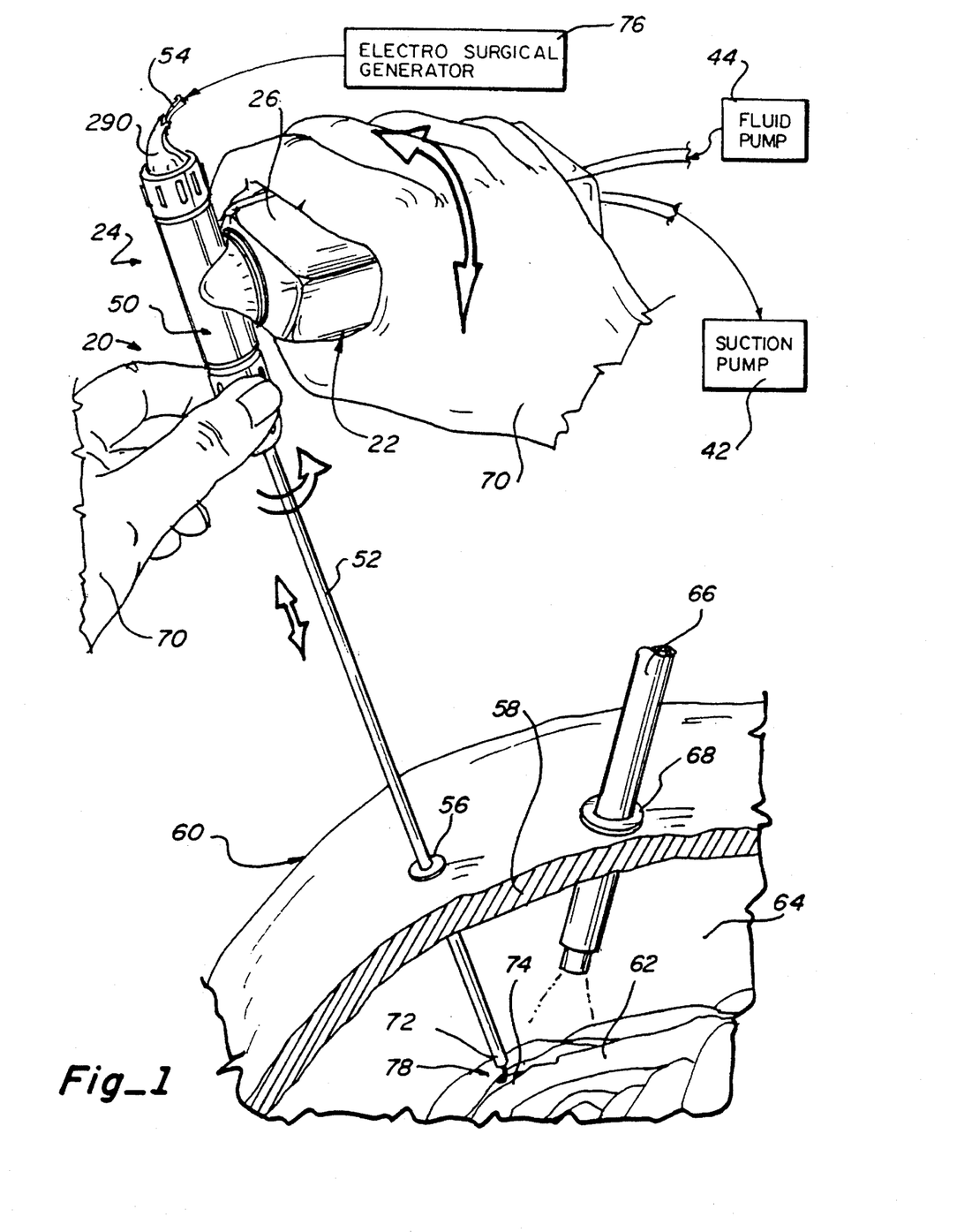
FIG. 1 is a perspective view showing use of an irrigator/aspirator surgical probe of the present invention in laparoscopic surgery within an abdominal cavity that is shown in a partially broken away illustration.

To use the probe 20, the probe tube 52 is inserted through a cannula 56 placed through a layer 58 of skin and muscle of a patient 60, usually in the abdominal region of the patient, as is shown in FIG. 1. An insufflator (not shown) pumps pressurized gas into the space between the skin and muscle layer 58 and the internal organs 62 to form an internal body cavity 64, typically an abdominal cavity. A combination light source and camera device 66 is inserted through a second cannula 68 placed through the skin and muscle layer 58. The light source of the device 66 illuminates the internal cavity 64 and the camera sends signals to a video monitor (not shown) by which a surgeon 70 can observe the progress of the surgical procedure. With the aid of this light source and camera device 66, the surgeon 70 manipulates the handle assembly 22 to place a distal end 72 of the probe tube 52 an surgical site 74 and perform the surgical procedure. A third cannula (not shown) is also sometimes used to provide an opening for additional surgical instruments and/or to inflate the internal cavity.

During the surgical procedure, it is common for the surgeon to electrosurgically coagulate bleeding sites by applying radio frequency electrical energy from a conventional electrosurgical generator 76 through the cable 54 to the electrode 53. The electrical energy jumps from a distal end 78 of the electrode 53 to the tissue at the surgical site 74 and causes an electrocoagulative effect, as is well known.

It may also be necessary during the procedure for the surgeon to irrigate the surgical site 74 with a liquid or a gas fluid such as sterile saline or air. The irrigation fluid is supplied from the fluid delivery pump 44, conducted through the flexible hose 46, conducted through the valve assembly 28 by depression of one control button 32 or 34, conducted through the probe body 50 and into the probe tube 52, where it is conducted in an annular space 80 (FIGS. 3, 5 and 18) between the electrode 53 and the probe tube 52 to the distal end 72 of the probe tube. It may also be necessary to aspirate the surgical site 74. Aspiration is accomplished by depressing the other one of the control buttons 32 or 34 which opens the valve it controls in the valve assembly 28 to a suctioned flow of liquid or gas fluid. The aspirated fluid and debris is carried by the flow of aspirated fluid flow into the distal end 72 of the probe tube 52, along the annular space 80 between the electrode 53, into the interior of the probe body 50, through the valve assembly 28 and the hose 48 to the suction pump 42. Aspiration is frequently applied to remove blood from the surgical site 74, to remove irrigating fluids after they have been applied and to remove smoke in the internal cavity 64 after electrosurgery has been performed.

The handle assembly 22, the probe assembly 24 and the use of the surgical probe 20 are discussed in greater detail below.

As shown in FIGS. 2, 3, 5 and 15, the handle assembly 22 includes the handle 26 formed by a housing 82 upon which a grip structure 83 is formed. A front face 84 of the housing 82 has openings formed therein, to allow components of the valve assembly 28 to protrude therethrough. A front panel 86 connects to the housing 82 and continues the structure 83 which the surgeon grips by hand when using the surgical probe 20. The front panel 86 can be snap fitted by conventional tabs and receptacles (not shown) into and out of engagement with the housing 82 to cover the front face 84 of the housing.

Figure 5:
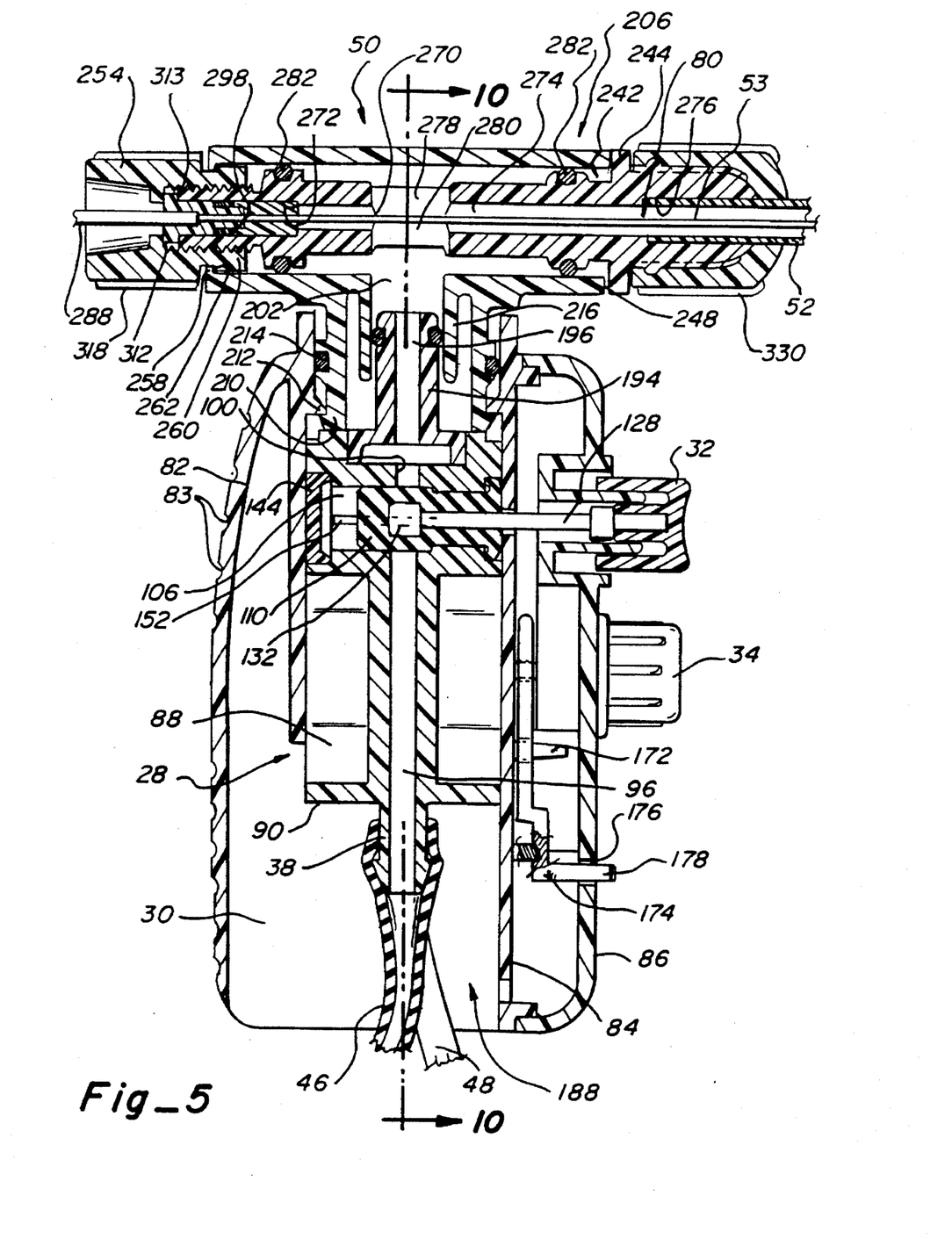
FIG. 5 is a sectional view taken substantially in the plane of line 5—5 of FIG. 4.
Figure 6:
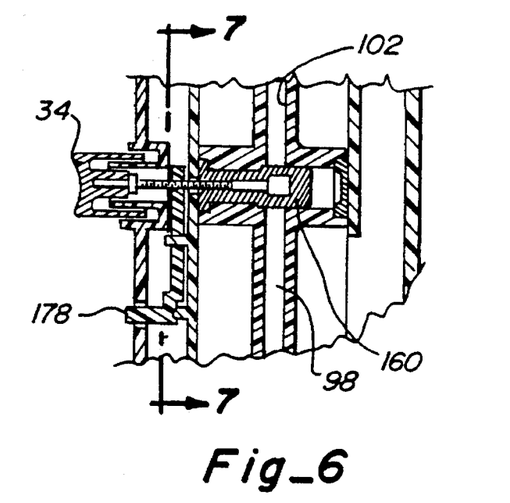
FIG. 6 is a partial sectional view taken substantially in the plane of line 6—6 of FIG. 4.
Figure 7:
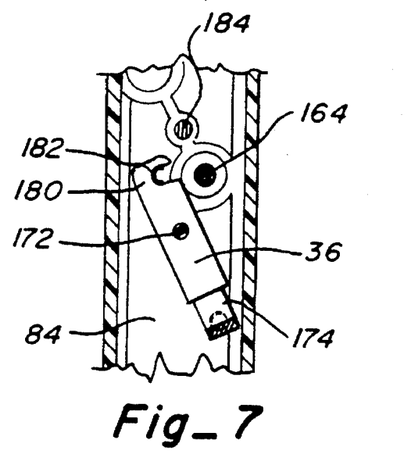
FIG. 7 is a partial sectional view taken substantially in the plane of line 7—7 of FIG. 6, showing a locking lever in a disengaged position.
Figure 7A:
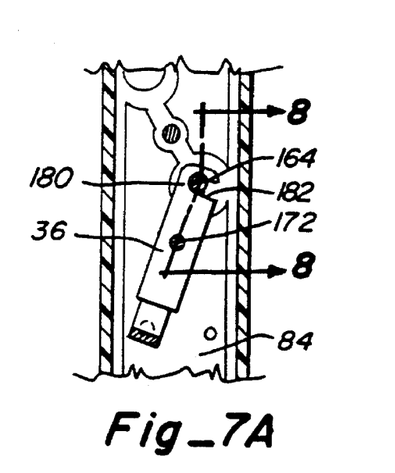
FIG. 7A is substantially the same view as FIG. 7, showing the locking lever in an engaged position.

The valve assembly 28 is located within the interior of the housing 82, as is best shown in FIG. 5. The valve assembly 28 includes a single valve body 88 which is preferably formed from a plastic material. Located on a bottom face 90 of the valve body 88 are the first and second connection ports 38 and 40, respectively. The connection ports 38 and 40 are connected to the fluid delivery pump 44 and to the suction pump 42 by the hoses 46 and 48 (FIG. 1). The first and second connection ports 38 and 40 communicate with a first and second internal passageway 96 and 98, respectively, formed in the valve body 88. The first and second internal passageways 96 and 98 communicate with a first and second flow port 100 and 102, respectively, located on a top face 104 of the valve body 88, as is also shown in FIG. 10.

Figure 10:
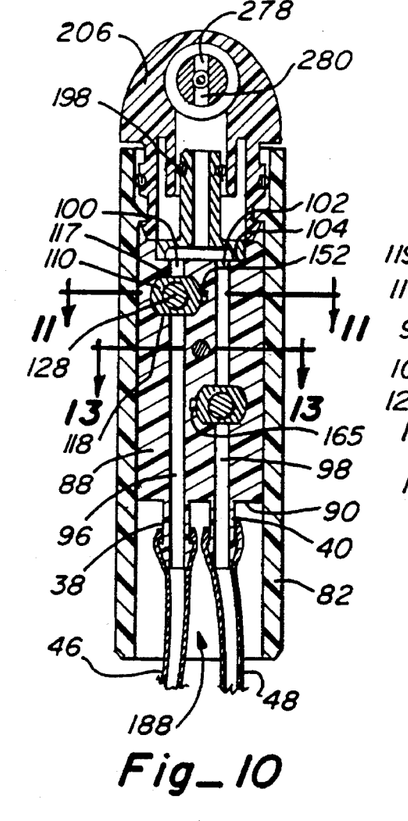
FIG. 10 is a sectional view taken substantially in the plane of line 10—10 of FIG. 5.
Figure 11:
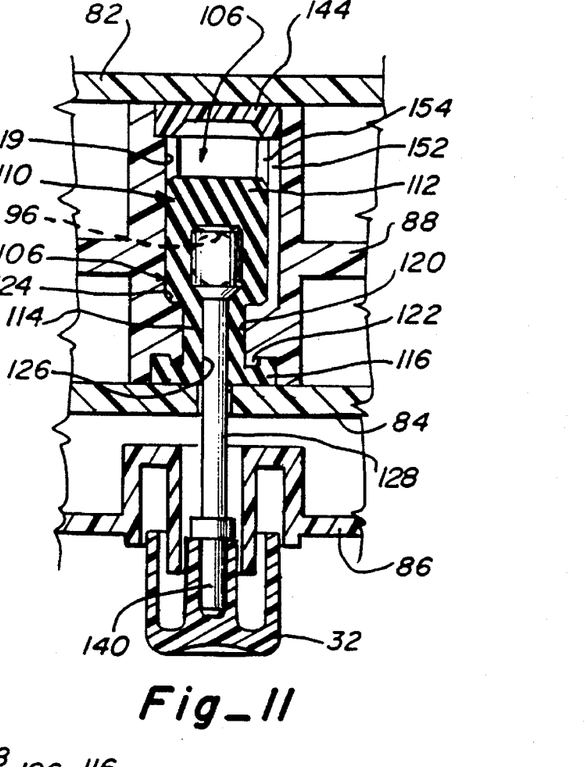
FIG. 11 is an enlarged partial sectional view taken substantially in the plane of line 11—11 of FIG. 10, showing a control valve in a closed, at rest or relaxed position.
Figure 12:
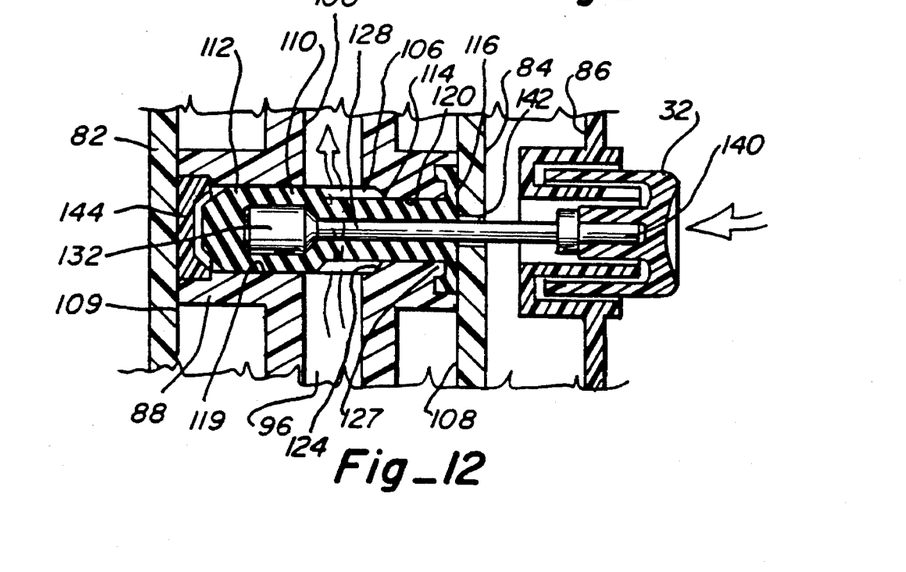
FIG. 12 is an enlarged portion of FIG. 5, showing a control valve in an open, stretched position.

A first internal valve bore 106 extends from a front face 108 to a back face 109 of the valve body 88, as is shown in FIGS. 5, 10, 11 and 12. The bore 106 intersects the first internal passageway 96. A first resilient valve member 110 is located in the first valve bore 106. The valve member 110 includes a plug portion 112, a neck portion 114, and a shoulder portion 116 (FIGS. 11 and 12). The plug portion 112 is generally cylindrical except that it has flattened upper and lower surfaces 117 and 118, respectively (FIG. 10). The neck portion is generally cylindrical. The plug portion 112 and the neck portion 114 are located in portions 119 and 120 of the valve bore 106 which are correspondingly shaped in cross-section. The shoulder portion 116 of the valve member 106 engages a lip 122 which surrounds the first internal bore 106 (FIG. 11) at the front face 108. The engagement of the lip 122 and the shoulder portion 116 in the first valve bore 106 prevent movement of the valve member 110 toward the back face 109. A second lip 124, separating the valve bore portions 119 and 120, contacts the plug portion 112 and prevents the plug portion from moving forward out of the valve bore once the valve member 110 is inserted in the valve bore 106. The valve member 110 is trapped in the valve bore by the lips 122 and 124. The first internal passageway 96 intersects the portion 119 of the bore 106 at a position slightly to the rear of the second lip 124, and at the flattened upper and lower surfaces of the valve bore portion 119.

The valve member 110 has an internal center bore 126 along its longitudinal axis, as is shown in FIGS. 11 and 12. The bore 126 extends through the shoulder portion 116, the neck portion 114 and partially into the plug portion 112 of the valve. The bore 126 has a slightly larger diameter in the plug portion 112 than in the neck portion 114 and shoulder portion 116 of the valve member 106.

A valve stem shaft 128 is positioned in the internal bore 126 of the valve member 110, as shown in FIGS. 11 and 12. An enlarged head 132 is formed on a rear end of the shaft 128. The enlarged head 132 is located in the enlarged portion of the internal bore 126 in the plug portion 112 of the valve member 110. The valve stem shaft 128 includes a smooth cylindrical portion 136 which extends through the reduced diameter portion of the internal bore 126 that extends through the neck portion 114 and shoulder portion 116 of the valve member 110. A threaded portion 138 of the valve stem shaft 128 extends forward of the smooth cylindrical portion 136. An end cap portion 140 is located on the outermost forward end of the valve stem shaft 128. The threaded portion 138 and the end cap portion 140 extend forward beyond the valve body 88 and through a circular opening 142 in the front face 84 of the housing 82. The control button 32 is attached to the end cap portion 140 of the valve stem shaft 128 on the exterior of the front panel 86. The front panel 86 includes a hole 143 through which the portions 138 and 140 of the valve stem shaft 128 extend. A configuration 145 surrounding the hole 143 allows the button 32 to be depressed.

Figure 8:
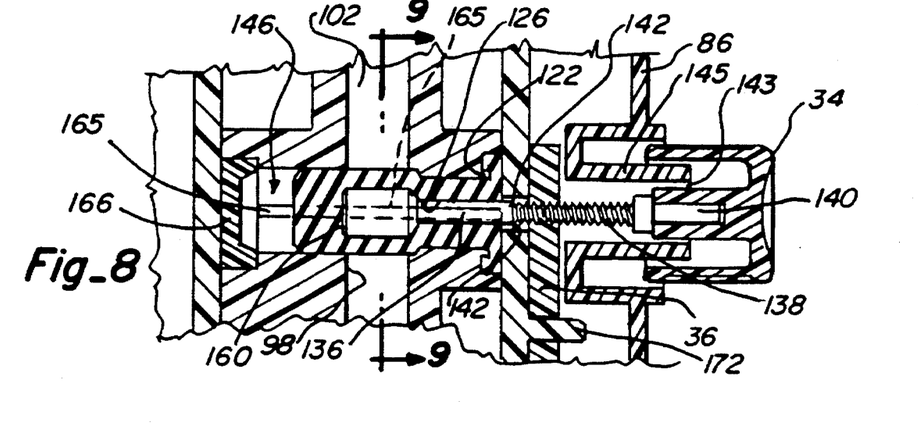
FIG. 8 is an enlarged partial sectional view taken substantially in the plane of line 8—8 of FIG. 7A.

The resilient valve member 110 is preferably formed of an elastomeric material. The elastomeric properties of the valve member 110 allow it to be stretched, after which it will rebound back to its original shape, thus acting as its own spring. Furthermore, the elastomeric properties of the plug portion 112 of the valve member completely seal against and occlude the openings of the first internal passageway 96 through the valve body 88, thus sealing the passageway 96 and causing the valve member 110 to act as a fluid sealing device in its relaxed position as shown in FIGS. 8 and 11.

The elastomeric properties of the valve 110 also allow the head portion 132 of the valve stem shaft 128 to be inserted through the smaller diameter portion of the bore 126 in the neck portion 114. After the head 132 is inserted to its rearwardmost position in the bore 126, the bore rebounds to its original shape and the valve stem shaft 128 is held in place in the valve member 110. The first control button 32 is press-fitted onto the end cap portion 140 of the valve stem 128.

Figure 9:
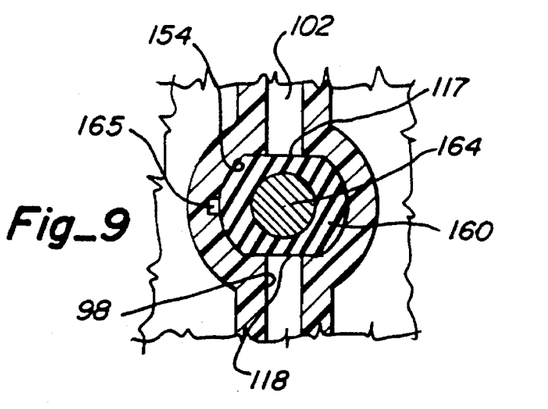
FIG. 9 is a partial sectional view taken substantially in the plane of line 9—9 of FIG. 8.

The length of the first internal bore 106 of the valve body 88 along its longitudinal axis is greater than the length of the valve member 110 (FIGS. 5 and 11). At the back face 109 of the valve body 88 a valve body cap 144 seals the rearward end of the internal bore 106 from the outside environment. When the valve member 110 is in its relaxed position (FIG. 11), a transition region 146 exists between the rearward face of the plug portion 112 and the forward face of the valve body cap 144. The transition region 146 provides room for the plug portion 112 of the valve 110 to move longitudinally in the internal bore 106. The flattened top side 117 and bottom side 118 (FIGS. 9 and 10) help to block and seal the internal passageway 96 when the valve member 110 is in the relaxed position (FIG. 11), thus substantially preventing the flow of fluid therethrough.

When the valve stem shaft 128 is moved along its longitudinal axis by operator depression of the control button 32, the elastomeric valve member 110 is stretched longitudinally. As is shown in FIG. 12, most of the stretching takes place in the neck portion 114. The plug portion 112 is moved rearward into the transition region 146. Upon displacing the plug portion 112 rearwardly from the second lip 124, the plug portion 112 no longer blocks the openings of the passageway 96 into the valve bore 106, and a fluid communication path is established. Fluid can flow through the first internal passageway 96 around the neck portion 114 of the valve member 110. The amount of fluid flow is dependent on the pressure of the fluid source and the size of the opening caused by the amount of rearward movement of the plug portion 112. Thus, the amount of fluid flow can be controlled by the amount of rearward displacement of the valve stem shaft 128 by depressing the button 32.

When the longitudinal force on the valve stem shaft 128 is reduced by releasing the button 32, the elastomeric properties of the valve 110 cause it to rebound back to the relaxed, at rest position (FIG. 8). In the relaxed position, the plug portion 112 has moved forward through the transition region 146 until the forward edge of plug portion 112 again contacts the second lip 124 of the valve bore 106. The flat surfaces 117 and 118 of the plug portion 112 again seal the internal passageway 96 against fluid flow therethrough.

A groove or relief channel 152 is formed in the valve body 88 in a wall 154 of the internal bore 106, as shown in FIGS. 10 and 11. This channel 152 runs longitudinally along the portion 119 of the valve bore 106 in which the plug portion 112 is located. The channel 152 equalizes the fluid pressure on both sides of the plug portion 112 as it moves forward and backward. With this channel 152, the plug 112 can be stretched toward the valve body cap 144 without a resulting increase in air pressure between the valve body cap 144 and the rear end of the valve member 110. Such an increase in air pressure would impede the smooth action of the valve member 110. Similarly, the plug portion 112 can easily move forward toward the second lip 124 when the valve member 110 relaxes. The channel 152 is formed in the valve bore 106 between the openings of the passageway 96 into the valve bore and the valve body cap 144. The plug portion 112 of the valve member 110 always contacts the channel 152 to prevent the fluid and debris passing through the passageway 96 from entering the channel 152.

The structure, nature and operation of the first valve member 110, the first internal passageway 96, the first internal valve bore 106, the first valve stem shaft 128, the first channel 152, the first control button 32 and the first valve body cap 144 have been described in detail, and are identical to the structure, nature and operation of a second valve member 160, the second internal passageway 98, a second internal valve bore 162, a second valve stem shaft 164, a second channel 165 (FIG. 9), the second control button 34 and a second valve body cap 166 (FIG. 2), respectively. Accordingly, details of the second valve are described since they are identical with the correspondingly named elements of the first valve.

The first and second internal passageways 96 and 98, respectively, extend generally parallel to each other through the valve body 88, as is shown in FIG. 10. The first and second valve bores 106 and 162 are also generally parallel to each other in the valve body 88, as well as being essentially perpendicular to the passageways 96 and 98. However, the two bores 106 and 162 are vertically offset from one another in their respective positions along the passageways 96 and 98. Further, as shown in FIG. 10, the relief channels 152 and 165 in each of the two bores 106 and 162, respectively, are located to the inside of the valve body 88.

The locking lever 36 is available for holding the second valve in an open or depressed position. As is shown in FIGS. 2, 4, 5, 6, 7, 7A and 8, the locking lever 36 is pivotally connected to the front face 84 of the valve body 88 by a pivot shaft 172. One end 174 of the locking lever 36 extends outward through a semicircular shaped slot 176 formed in the front panel 86. The end 174 forms a tab 178 which is accessible to pivot the lever 36 about the pivot shaft 172. Another end 180 (FIG. 7) of the locking lever 36 has a notch 182 formed in one side facing the threaded portion 138 of the valve stem shaft 164. The internal surface of this notch 182 is threaded at the same pitch as the threads on the threaded portion 138 of the valve stem shaft 164.

When the locking lever 36 is pivoted, the threaded notch 182 engages with the threaded portion 138 of the valve stem shaft 164, and the valve stem shaft is held in this position. The valve member 160 may be held at any position to which it has been depressed by the locking lever 36, thereby establishing a fixed open setting for the valve. The surgeon is relieved of maintaining pressure on the button 34. The button 34 and valve stem shaft 164 can be turned to finely adjust the open position of the second valve, because the valve stem shaft 164 will rotate in the bore 162 in the valve member 160. The flat sides 117 and 118 (FIG. 10) of the valve member 160 prevent it from rotating in the valve bore 162. When the operator disengages the locking lever 36 by moving the tab 178 to pivot the lever and move the threaded notch 182 away from the threaded portion 138 of the valve stem shaft 164, the valve member 110 is free to operate as previously described.

Thus, the surgeon can actuate the valve member 160 to a desired position, lock that position with the locking lever 36 and then make further adjustments as necessary. Alternatively, the surgeon can begin by pivoting the locking lever 36 to hold the valve member 160 in the closed position and then turn the valve stem shaft 164 and button 34 until the desired open position is achieved.

Figure 13:
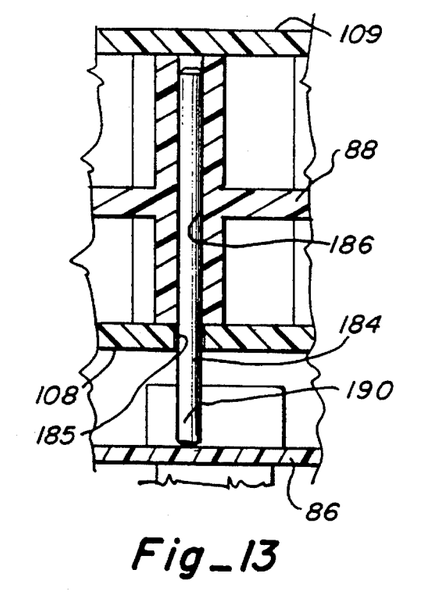
FIG. 13 is an enlarged partial sectional view taken substantially in the plane of line 13—13 of FIG. 10, showing a snap pin hidden under a front panel of a handle of the surgical probe.
Figure 14:
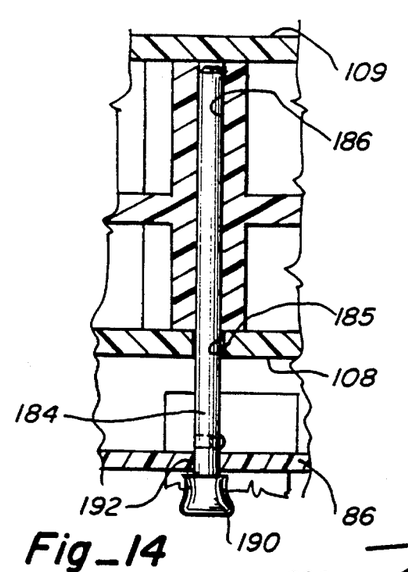
FIG. 14 is substantially the same view as FIG. 13, showing another arrangement with a snap pin extending through a front panel of a handle of the surgical probe.
Figure 15:
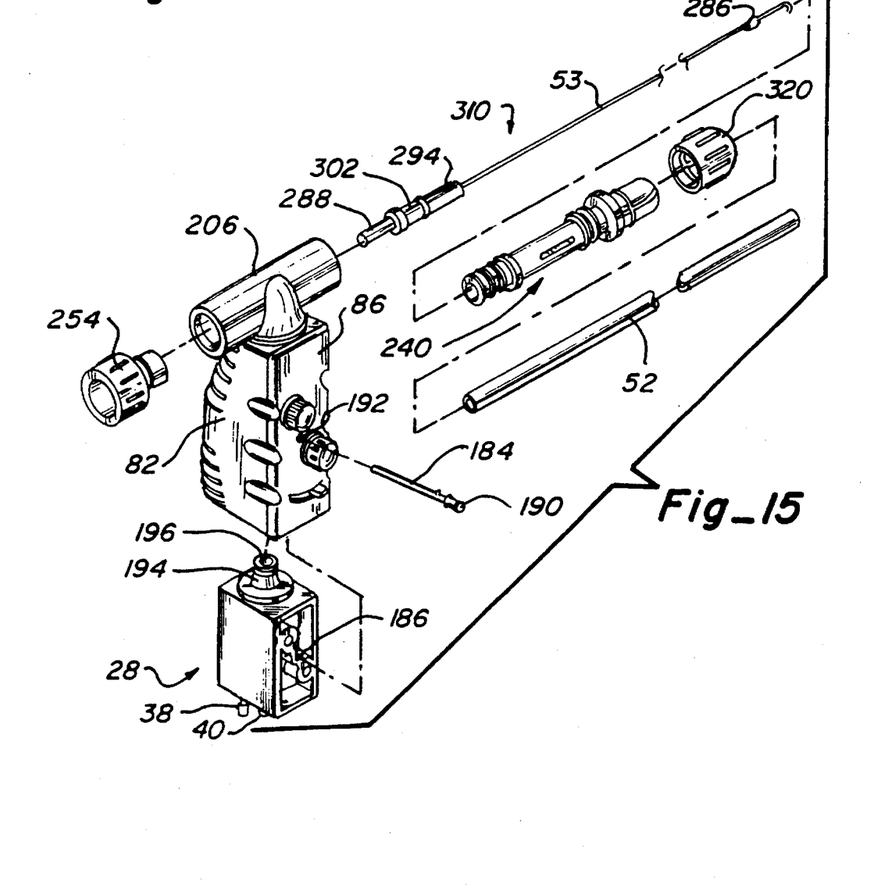
FIG. 15 is an exploded perspective view of the surgical probe shown in FIGS. 1, 2 and 3, with the handle assembly rotated relative to the probe assembly and illustrating the removable and replaceable nature of the valve assembly using the snap pin arrangement shown in FIG. 14.

The valve body 88 is held in place in the handle 26 by a snap pin 184 inserted through an opening 185 in the front face 108 of the housing 82 and into a pin receptacle 186 in the valve body 88, as is shown in FIGS. 13, 14 and 15. When the valve stem shafts 110 and 160 and the snap pin 184 are removed, the valve body 88 is no longer attached to the housing 82. The valve body 88 then can be easily removed through an open bottom end 188 (FIG. 5) of the housing, as is illustrated in FIG. 15.

FIGS. 13 and 14 show two alternative arrangements for holding the valve body 88 using the snap pin 184. In one arrangement (FIG. 13) a head 190 of the snap pin 184 is hidden under the front panel 86. This arrangement is preferably used when the entire probe 20 including the valve body 88 will be disposed of after each surgical use. When the probe is disposable, as many of the other components of the surgical probe as realistically possible will be formed from low-cost plastic. In the other arrangement (FIG. 14) a hole 192 is formed through the front panel 86 and the snap pin 184 is inserted through the opening 185 and into the receptacle 186 of the valve body 88. The head 190 of the snap pin is visible and accessible from the exterior of the handle assembly 22. This arrangement is used where it is desirable to remove, dispose of and replace the valve body 88 after each use. The remainder of the surgical probe must be sterilized before subsequent use. Where the valve body is disposable and the remaining portions of the surgical probe are re-useable, the present invention will usually have many non-disposable components, other than the valve body 88, which are able to withstand sterilization.

A confluence chamber member 194 is attached, preferably by a sealing adhesive, to the top face 104 of the valve body 88, as is shown in FIGS. 2, 5, 10 and 15. The confluence chamber 194 establishes a common communication channel between the two internal passageways 96 and 98 of the valve body 88 and an upper opening 196 formed in the confluence chamber 194. Fluid communication with the probe assembly 24 is established through the opening 196. An O-ring seal 198 is attached surrounding the opening 196 on a neck portion 199 of the confluence chamber 194. The O-ring 198 seals the confluence chamber 194 to the probe body 50 of the probe assembly 24. The confluence chamber 194 conducts the gas and liquid fluid delivered through the valves during irrigation and aspiration of the surgical site, as determined by the surgeon's actuation of valves by the control buttons 32 and 34.

The fluid conducted from or to the confluence chamber during irrigation and aspiration enters and leaves from an interior chamber 202 of the probe body 50, as shown in FIG. 5. The interior chamber 202 of the probe body communicates with the annular space 80 between the probe tube 52 and the electrosurgical electrode 53 or some other surgical instrument, such as a gas-assisted electrosurgical tubing and nozzle assembly, a surgical laser optical bundle or a mechanical surgical instrument, for example (none of which are shown).

Figure 2:
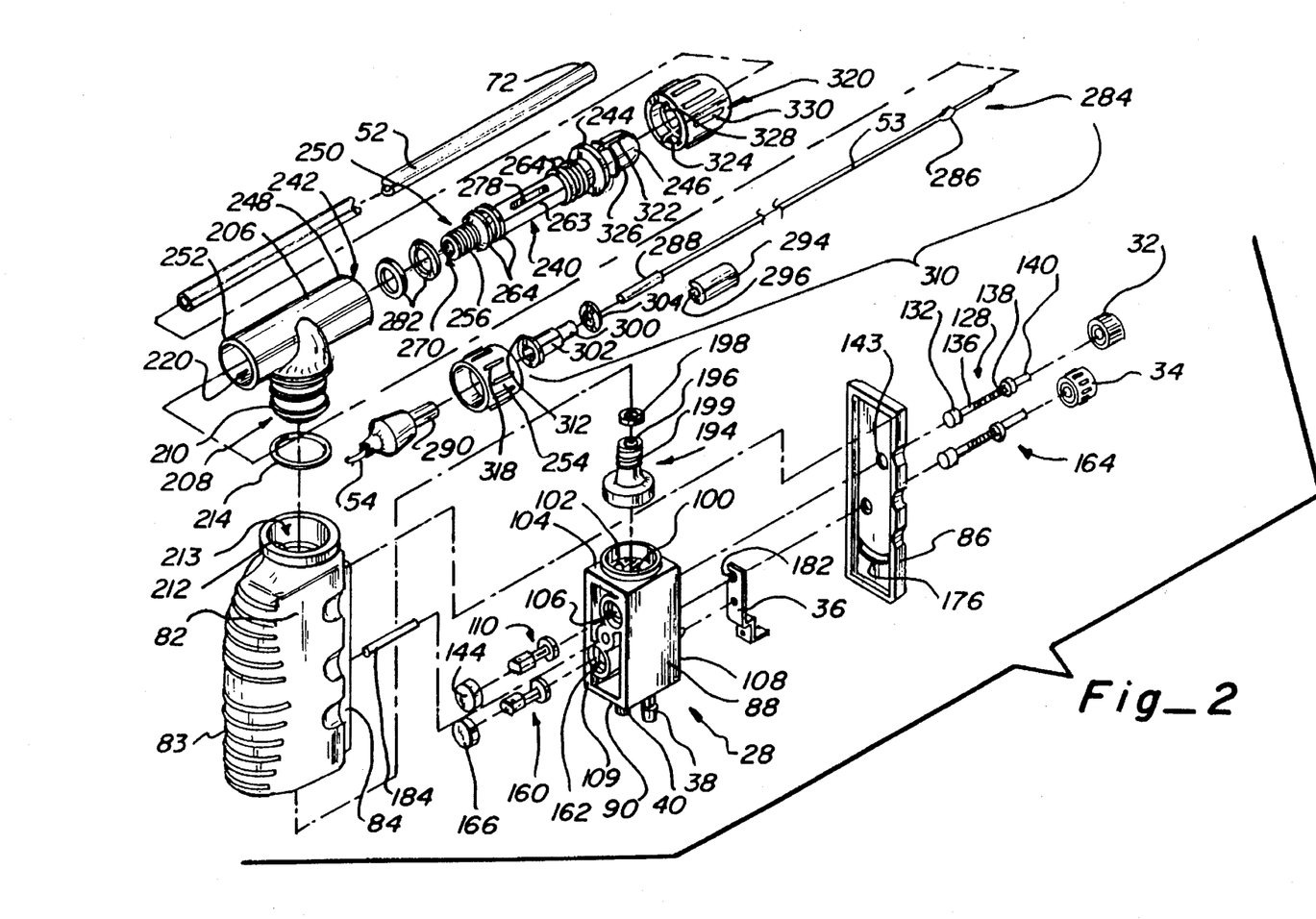
FIG. 2 is an exploded perspective view of the components of the surgical probe shown in FIG. 1.

The probe body 50 of the probe assembly 24 includes a T-shaped housing 206, as shown in FIGS. 2, 5 and 15. The housing 206 includes a port 208 which engages with and fits within the handle assembly 22. On the exterior of the port 208 is a resilient lip 210 which snaps into engagement with a lip 212 in an upper opening 213 of the housing 82 (FIG. 5). An O-ring 214 is located on the exterior of the port 208 to engage with and seal against the housing 82 at the opening 213.

An integral sleeve 216 (FIG. 5) of the T-shaped housing 206 ms located in the interior of the port 208 and extends toward the handle assembly. The sleeve 216 engages the O-ring 198 on the neck portion 199 of the confluence chamber 194 to establish the primary seal between the handle assembly 22 and the probe assembly 24. The O-ring 214 between the port 208 and the housing 82 functions as a secondary seal to prevent leakage between the handle assembly and the probe assembly. Once the T-shaped housing 206 is connected in place on the handle housing 82, the housing 206 may be rotated freely relative to an axis through the handle assembly 22 and handle 26, as shown in FIGS. 1, 5 and 15, since the O-rings 198 and 214 permit this relative rotational movement while maintaining the seal between the handle assembly and the probe assembly.

The hollow interior of the sleeve 216 is part of the interior chamber 202 of the housing 206 and communicates with the interior of the confluence chamber 194. The interior chamber 202 of the T-shaped spool housing 206 also includes a large, internal bore 220 through which many of the remaining components of the probe assembly 24 are attached to and within the spool housing 206.

A cylindrical electrode spool 240 is inserted into a front end 242 of the internal bore 220 of the housing until an annular protruding lip 244 near a front end 246 of the electrode spool 240 abuts a ring-shaped front face 248 of the spool housing 206, as is shown in FIGS. 2 and 5. In this position, a rear end 250 of the electrode spool 240 protrudes slightly rearwardly outward from the internal bore 220 beyond a rear face 252 of the spool housing 206.

The spool 240 is held in this position by a nut 254 which is threaded on an external thread 256 that is formed on the rear end 250 of the electrode spool 240. A lip 258 extends inwardly at the open rear end of the housing 206. The nut 254 includes a forward projecting internal sleeve 260. An outer projecting annular ring 262 is located on the forward end of the sleeve 260, and the ring 262 is forced forward past the lip 258 to snap fit the nut 254 to the rear end of the housing 206. The snap fit between the lip 258 and the ring 262 and sleeve 260 allows the nut 254 to freely rotate in its attachment to the rear of the spool housing 206. When the nut 254 is loosely tightened on the threads 256 of the electrode spool 240, a slight axial tolerance exists between the protruding lip 244 near the front end of the spool and the front face 248 of the housing 206 and/or between the nut 254 and the rear face 252 of the housing 206. This axial tolerance allows rotation of the electrode spool 240 relative to the housing 206.

Integrally formed into an outer surface 263 of the electrode spool 240 are a first and a second pair of support collars 264. When the electrode spool 240 is located in the spool housing 206, the support collars 264 are located near each end of the spool housing 206. The support collars contact a cylindrical wall internal bore 220 of the housing 206. Due to the relatively smooth surface of the internal bore 220 and the outer circular shape of the support collars 264, the electrode spool 240 may also freely rotate within the internal bore of the spool housing on the support collars 264.

The electrode spool 240 has a hollow interior channel 270 formed axially through the spool 240. The interior channel 270 is formed in three generally cylindrically shaped sections. A rear section 272 of the channel 270 has the largest diameter of the three sections. A center section 274 of the channel 270 has the smallest diameter of the three sections. A front section 276 of the channel has a diameter larger than the center section 274 and smaller than the rear section 272. The probe tube 52 has an outer diameter sufficient to snugly fit within the diameter of the front section 276 of the channel 270. The probe tube 52 is formed of a poltruded, non-conductive, composite material, and is connected to the front section 276 of the internal channel 270 as shown in FIG. 5, preferably with an adhesive.

Two communication ports 278 and 280 are formed in the spool 240 between the pairs of support collars 264 and extend from the outer surface 263 of the spool to the center section 274 of the interior channel 270, as is shown in FIGS. 2 and 5. The communication ports 278 and 280 establish a communication path between the interior chamber 202 of the spool housing 206 and the interior channel 270 of the electrode spool 240. An 0-ring 282 is placed between each of the two pairs of support collars 264 to establish a seal between the exterior of the spool 240 and the internal bore 220 at the location of the support collars 264. The seals established by the O-rings 282 are located in front of and behind the location where the sleeve 216 opens from the interior chamber 202 into the opening 196 of the confluence chamber. As a result, the fluid communication to and from the handle assembly 22 through the confluence chamber 194 is confined to the interior chamber 202 between the O-rings and to the interior channel 270 of the spool through the communication ports 278 and 280.

Figures 3, 18:
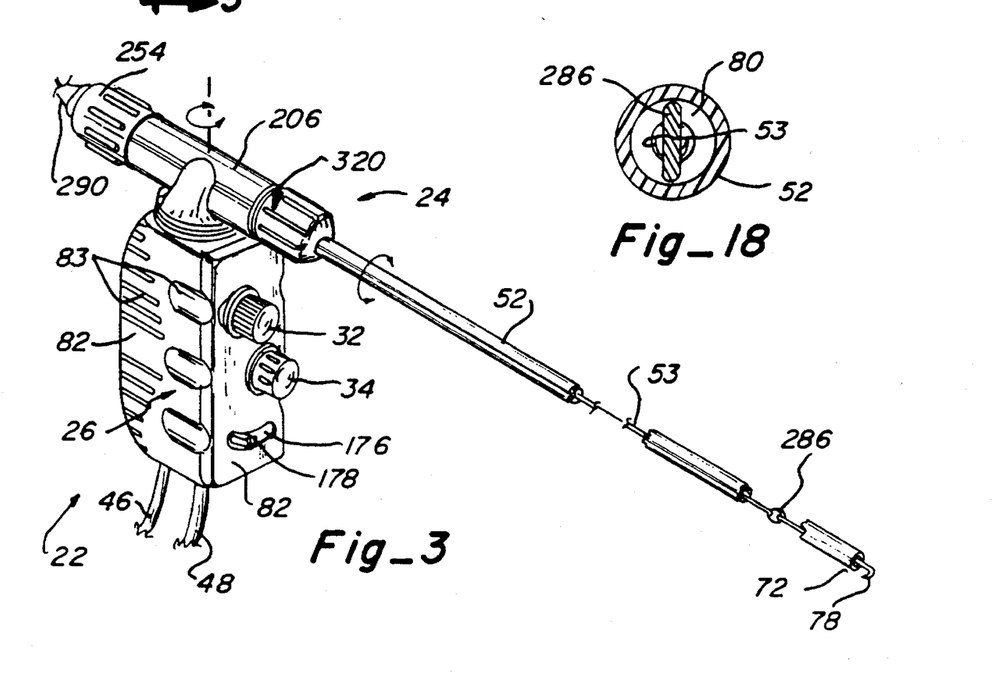
FIG. 3 is a perspective view of the surgical probe shown in FIGS. 1 and 2.
FIG. 18 is a transverse section view taken substantially in the plane of line 18—18 of FIG. 17.
Figures 4, 16, 17:
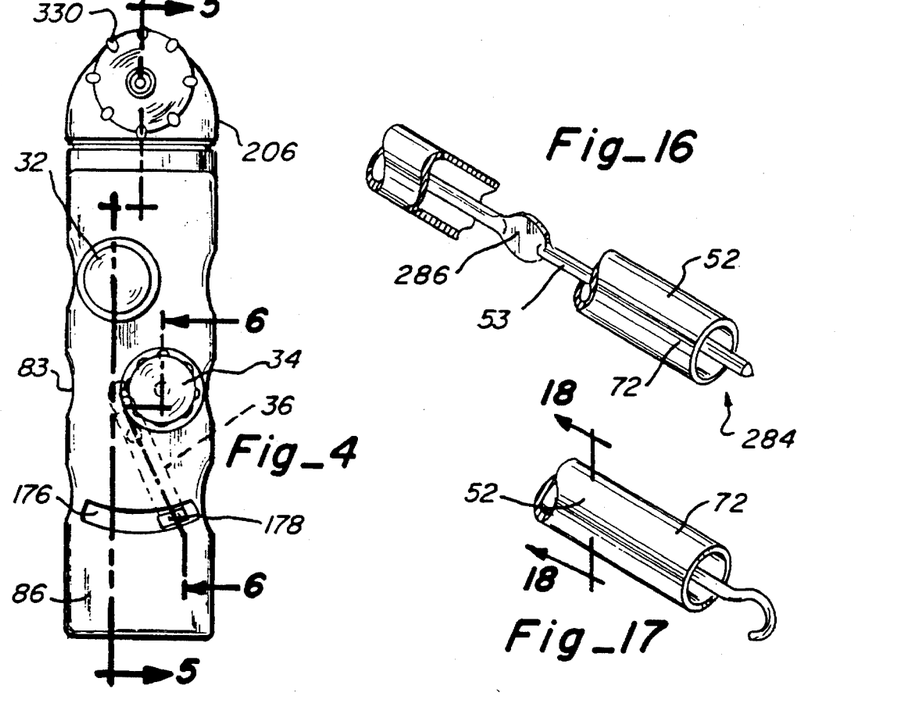
FIG. 4 is a front elevation view of the surgical probe shown in FIG. 3 with portions broken away.
FIG. 16 is a perspective view, with a portion broken away, illustrating the distal end of a probe tube of a probe assembly of the surgical probe shown in FIGS. 1, 2 and 3.
FIG. 17 is a perspective view similar to that shown in FIG. 16 illustrating a J-hook end formed on an electrode extending from the distal end of the probe tube, as an alternative to the pointed end of a straight electrode shown in FIG. 16.

The electrode 53 is preferably inserted into the electrode spool 240 as is shown in FIGS. 2, 5 and 15. Preferably, the electrode 53 is a solid, elongated and stiff electrical conductor with a tip 284 having a needle or some other configuration (FIGS. 16 or 17) at its distal end, although a gas conducting tubing with a nozzle and electrode assembly such as that employed in gas assisted electrocoagulation, described in U.S. Pat. No. 4,781,175, could also be employed. The electrode 53 is maintained in a centered position relative to the non-conductive probe tube 52 by an enlarged flat portion 286 (FIG. 16) formed near its distal end. The flat portion 286 contacts the inside of the probe tube 52 and holds the distal end of the electrode 53 in a centered position relative to the distal end 72 of the probe tube, as is shown in FIG. 18. Since the rear end of the electrode 53 is also maintained in an axially centered position in the electrode spool as explained below, the electrode 53 extends coaxially along the probe tube 52 and through the probe assembly 24.

Attached to the rear of the electrode 53 is a female receptacle tube 288 which receives a male banana-clip electrical connector 290 connected to the end of a cable 54 from the electrosurgical generator 76, as is shown generally in FIGS. 1 and 3 and more specifically in FIGS. 2, 5 and 15.

The hollow receptacle tube 288 slips over, and is electrically connected with (preferably by soldering) the rear end of the electrode 53 (FIG. 5). Mechanically attached near the rear end of the electrode 53 and in front of the tube 288 is a collar 294. The collar 294 includes a radially extending slot 296 (FIGS. 2 and 15) to allow the collar 294 to be placed over the tube 288 from the side. The collar 294 has an enlarged end receptacle 298 (FIG. 5) in which to receive a reduced diameter sleeve portion 300 of an insert 302. The insert 302 is positioned over the tube 288 from the rear and attached thereto, preferably by an adhesive. An O-ring 304 is positioned over the sleeve portion between a forward facing shoulder of the insert and a rearward facing end surface of the collar 294. The electrode 53, the receptacle tube 288, the collar 294, the insert 302 and the 0-ring 304 make up an electrode assembly 310 (FIG. 2).

The electrode assembly 310 is inserted into the rear of the channel 270 of the electrode spool 240 until a protruding lip 312 on the insert 302 abuts the rear end of the spool 240, as is shown in FIG. 5. Thereafter the electrode spool 240 is inserted into the internal bore 220 from the front end of the spool housing 206. The nut 254 is threaded onto the threads 256 at the rear end of the electrode spool 240. A forward facing shoulder 313 on the nut 254 contacts the lip 312 and holds the insert 302 and hence the electrode assembly 310 in place relative to the electrode spool 240. As the nut 254 is tightened more, the electrode spool is drawn to the rear, and the lip 244 contacts the front face 248 of the spool housing 206, thus also holding the electrode spool 240 and the electrode assembly 310 firmly in place in the spool housing 206.

The collar 294 and the cylindrical portion of the insert 302 in front of the lip 312 and behind the sleeve portion 300 fit snugly into the rear section 272 of the interior channel 270 to locate the electrode 53 axially within the interior channel of the electrode spool 240, as is shown in FIG. 5. Further forward movement of the electrode assembly 310 relative to the electrode spool 240 is prevented by contact of the front end of the collar 294 against the shoulder of the electrode spool at the transition from the rear section 272 to the center section 274 of the interior channel 270. The axial force applied from the nut 254 to the insert 302 is transferred through the O-ring 304 to the collar 294 and to the electrode spool 240. The O-ring 304 between the insert 302 and the collar 294 is slightly compressed to establish a seal with the wall of the rear section 272 of the interior channel, thereby preventing gas and liquid from exiting from the rear of the probe assembly 24. Held together in this manner, the needle tip 284 of the electrode 53 is located at a predetermined position relative to the distal end 72 of the probe tube 52.

Tightening of the nut 254 on the electrode spool 240 will firmly restrain the electrode spool against the spool housing 206, thus substantially preventing the electrode spool and electrode assembly 310 from rotating about their longitudinal axes. Of course, when the locking nut is loosened, the electrode spool and the electrode assembly can be freely rotated. Eight raised longitudinal ridges 318 on the exterior of the nut 254 aid in grasping and turning the nut.

A knob 320 is attached to the front end 246 of the electrode spool 240 to allow the surgeon to easily and conveniently turn the spool 240 and the electrode assembly 310 relative to the spool housing 206. The knob 320 is formed as a cap-like structure having an interior shape to slide over and fit on the bulbous front end 246 of the electrode spool, as is shown in FIGS. 2, 5 and 15. A pair of diametrically opposed and outward protruding longitudinal ridges 322 are formed on the outer surface of the bulbous front end 246. Two longitudinal grooves 324 are formed in the interior of the knob 320 to mate and engage with the longitudinal ridges 322 on the front end of the electrode spool 240. An annular ridge 326 is also formed on the bulbous front end 246. The annular ridge 326 lies in a plane parallel to and slightly forward of the protruding lip 244 on the front end 246 of the electrode spool. An annular ring groove 328 extends into the interior of the knob 320. The ring groove 328 is located at a position which mates and engages with the annular ridge 326 on the electrode spool when the knob 320 is pressed on to the front end 246 of the electrode spool. The mating engagement of the ring groove 328 and the annular ridge 326 prevents the knob 320 from easily disengaging with the front end 246 once it has been snapped on. The mating engagement of the longitudinal ridges 322 and grooves 324 allows torque applied to the knob to be transferred to the electrode spool. The knob 320 preferably has eight raised, longitudinal ridges 330 to assist in grasping and turning the knob 320.

To use the surgical probe 20, it is connected to the electrosurgical generator 76 with the cable 54 and the connector 290, as is shown in FIG. 1. The surgical probe is also connected to a source of suction such as the suction pump 42 and to a source of fluid such as the fluid delivery pump 44. The valves are used to control the delivery of fluid for irrigation and the application of suction for aspiration. The surgeon twists the handle assembly 22 relative to the probe assembly 24 until a comfortable position is achieved. The distal end 72 of the probe tube 52 is located at the desired surgical site. The buttons 32 and 34 are depressed to irrigate or aspirate the surgical site. The electrosurgical generator 76 is energized to deliver RF electrical energy through the electrode 53 and thereby create an electrocoagulative effect at the surgical site 74.

The valve members 110 and 160 are elastomeric and their inherent resiliency acts as a return spring and as an effective seal. The self returning aspects of the valves are important in reducing the number of working parts and potential sources of mechanical failure. The resiliency achieves a good fluid seal even when small pieces of debris move through the valve assembly. Should a small piece of debris be trapped at one of the openings to the internal passageways 96 and 98 when the valve is closed, the resilient material of the valve member is usually successful in deforming around the debris and still establishing an effective seal.

Further, one of the valves can be locked in any selected position by actuation of the locking lever 36. Fatigue and discomfort to the surgeon is avoided because the surgeon is relieved of the task of continually depressing the control button for the valve. Very precise regulation of the degree of opening or closing of the valve is also attainable because of the threaded engagement of the locking lever 36 and the threaded portion 138 of the valve stem shaft.

Part of the surgical probe 20 can be made reusable by allowing the valve assembly 28 to be removed and disposed of while another new valve assembly can be inserted after the remaining portions of the probe have been sterilized. Thus, the probe need not be made wholly reusable or wholly disposable, although the construction of the probe admits to convenient disposable construction.

Due to the rotatable connection of the probe assembly 24 and the handle assembly 22, the probe assembly can be freely rotated about the handle assembly. The surgeon can twist the handle assembly 22 relative to the probe tube 52, as shown in FIG. 1, to maximize comfort, provide for right handed and left handed use of the probe, and achieve better control over the conduct of the surgical procedure.

The electrode spool 240 and thus the electrode 53 may be rotated about their longitudinal axes by loosening the locking nut 254 and twisting the electrode spool knob 320 as necessary. The surgeon is able to adjust the position of a non-symmetrical electrode, such as a j-hook electrode.

By removing the locking nut 254, the entire electrode assembly 310 can be easily removed from the probe assembly 24. This allows the surgeon to change to different types of electrodes while using only one probe tube.

A presently preferred embodiment of the present invention has been described above with a degree of specificity. It should be understood, however, that this degree of specificity is directed toward the preferred embodiment. The invention itself is defined by the scope of the following claims.

The invention claimed is:

1. A surgical probe by which to apply irrigation or aspiration fluid from one of a source of irrigation or aspiration fluid to a surgical site, comprising:

an elongated probe tube through which the irrigation or aspiration fluid flows to and from the surgical site;

a handle connected to the probe tube by which to hold the probe with finger pressure and manipulate the probe tube at the surgical site by the handle during a surgical procedure;

means within the handle defining a fluid communication path extending through the handle and communicating with the probe tube at one end of the communication path;

means for connecting the other end of the communication path to the source of irrigation or aspiration fluid;

a valve assembly located within the handle and connected in the communication path between the ends of the communication path to control the flow of fluid through the communication path to and from the probe tube;

the valve assembly including a moveable valve member located within the communication path;

the valve member moveable between a closed position where the fluid flow in the valve assembly and through the communication path is terminated and an open position where the fluid flow in the valve assembly and through the communication path is established;

the valve assembly further including means applying a biasing force on the valve member to bias the valve member normally into the closed position, the biasing force resisting movement of the valve member into the open position an actuator connected to the valve member and extending to the exterior of the handle by which to apply finger pressure to overcome the biasing force and move the valve member to the open position; and a locking device connected to the handle and selectively moveable by finger pressure into engagement with the actuator to hold the valve member in an open position and to reisist the biasing force tending to move the valve member to the normally closed position.

2. A surgical probe as defined in claim 1 wherein:

the valve assembly is removable from the handle to allow selective replacement of the valve assembly after use.

3. A surgical probe as defined in claim 1 wherein:

the handle is rotatably connected to the probe tube; and further comprising:

a rotational seal located within the handle and in the communication path to maintain fluid flow through the communication path upon rotation of the handle relative to the probe tube when the valve member is in the open position.

4. A surgical probe as defined in claim 1 further comprising:

an elongated electrode positioned within the probe tube and through which electrical energy is applied from a distal end of the electrode to achieve an electrosurgical effect at a surgical site.

5. A surgical probe as defined in claim 4 further comprising:

the electrode is selectively removable from the probe tube.

6. A surgical probe by which to apply irrigation or aspiration fluid from one of a source of irrigation or aspiration fluid to a surgical site, comprising:

an elongated probe tube through which the irrigation or aspiration fluid flows to and from the surgical site;

a handle connected to the probe tube to allow manipulation of the probe by the handle during a surgical procedure;

a valve assembly located within the handle and operative for controlling the flow of fluid through the probe tube, the valve assembly including means adapted for connecting the valve assembly to the source of irrigation or aspiration fluid;

the valve assembly including a valve member normally biased into a closed position to terminate the flow of fluid through the probe tube, said valve member selectively moveable from the closed position to an open position to establish the flow of fluid through the probe tube;

a locking device connected to the handle and selectively moveable independently of the movement of the valve member into a holding position where the valve member is restrained against further movement from the position the valve member occupied when the locking device was moved into the holding position, the locking device also selectively moveable independently of the movement of the valve member into a free position where movement of the valve member is not inhibited by the locking device; and the locking device including a portion which protrudes to the exterior of the handle and which is contactable by finger pressure to move the locking device between the holding and the free positions.

7. A surgical probe as defined in claim 6 wherein:

the valve assembly is removable from the handle to allow selective replacement of the valve assembly after use.

8. A surgical probe as defined in claim 6 wherein:

the handle is rotatably connected to the probe tube; and further comprising:

a rotational seal located within the handle and surrounding the fluid flow within the handle to maintain fluid flow through the handle upon rotation of the handle relative to the probe tube when the valve member is in the open position.

9. A surgical probe as defined in claim 6 further comprising:

an elongated electrode positioned within the probe tube and through which electrical energy is applied from a distal end of the electrode to achieve an electrosurgical effect at a surgical site.

10. A surgical probe as defined in claim 9 further comprising:

the electrode is selectively removable from the probe tube.

11. A surgical probe by which to apply irrigation or aspiration fluid from one of a source of irrigation or aspiration fluid to a surgical site, comprising:

an elongated probe tube through which the irrigation or aspiration fluid flows to and from the surgical site;

a handle connected to the probe tube to allow manipulation of the probe by the handle during a surgical procedure;

a valve assembly located within the handle and operative for controlling the flow of fluid through the probe tube, the valve assembly including means adapted for connecting the valve assembly to at least one source of irrigation or aspiration fluid;

the valve assembly including a valve member moveable between a closed position where the fluid flow within the probe tube is terminated and an open position where the fluid flow is established to the source of irrigation or aspiration fluid;

a locking device connected to the handle and selectively moveable between a holding position where the valve member is held in the position it occupied when the locking device was moved into the holding position and a free position where movement of the valve member is not inhibited by the locking device;

the locking device including a tab-like portion which protrudes to the exterior of the handle and which is contactable to move the locking device between the holding and the free positions;

a shaft connected to the valve member and operative for moving the valve member between the open and closed positions, the shaft extending from the valve assembly; and wherein:

the locking device contacts the shaft in the holding position to maintain the position of the shaft.

12. A surgical probe as defined in claim 11 wherein:

the shaft has an externally threaded region in which it is contacted by the locking device; and the locking device includes a threaded portion which contacts the threaded region of the shaft when the locking device is positioned in the holding position.

13. A surgical probe as defined in claim 12 wherein:

the threads on the threaded region mesh with the threads on the threaded portion of the shaft;

the engagement of the threaded portion and the threaded region allows rotation of the shaft to establish longitudinal movement of the shaft while the locking portion is in contact with the shaft when the locking device is in the holding position;

the shaft extends to the exterior of the handle to allow the shaft to be rotated; and longitudinal movement of the shaft moves the valve member.

14. A surgical probe as defined in claim 12 wherein:

the locking device includes a locking lever which is pivotably connected to the housing;

the locking lever includes a notch which contacts the threaded portion of the shaft and which forms the threaded portion of the locking device; and the locking lever includes the tab-like portion.

15. A surgical probe as defined in claim 11 wherein:

the valve assembly is removable from the handle to allow selective replacement of the valve assembly after use; and the shaft is disconnectable from the valve member to allow the valve assembly to be removed from the handle.

16. A surgical probe as defined in claim 11 wherein:

the valve assembly is removable from the handle to allow selective replacement of the valve assembly after use.

17. A surgical probe as defined in claim 11 wherein:

the handle is rotatably connected to the probe tube; and further comprising:

a rotational seal located within the handle and surrounding the fluid flow within the handle to maintain fluid flow through the handle upon rotation of the handle relative to the probe tube when the valve member is in the open position.

18. A surgical probe as defined in claim 11 further comprising:

an elongated electrode positioned within the probe tube and through which electrical energy is applied from a distal end of the electrode to achieve an electrosurgical effect at a surgical site.

19. A surgical probe as defined in claim 18 further comprising:

the electrode is selectively removable from the probe tube.

\* \* \* \* \*